(12) United States Patent
Wollschleger

(10) Patent No.: US 10,387,620 B1
(45) Date of Patent: Aug. 20, 2019

(54) MEDICATION SORTING AND PACKAGING SYSTEM AND METHOD

(71) Applicant: Exact Care Pharmacy, LLC, Valley View, OH (US)

(72) Inventor: Dale M. Wollschleger, Solon, OH (US)

(73) Assignee: Exact Care Pharmacy, LLC, Valley View, OH (US)

( * ) Notice: Subject to any disclaimer, the term of this patent is extended or adjusted under 35 U.S.C. 154(b) by 91 days.

(21) Appl. No.: 15/296,576

(22) Filed: Oct. 18, 2016

Related U.S. Application Data

(60) Provisional application No. 62/243,329, filed on Oct. 19, 2015.

(51) Int. Cl.
*G06F 19/00* (2018.01)
*A61J 7/00* (2006.01)

(52) U.S. Cl.
CPC ........ *G06F 19/3456* (2013.01); *A61J 7/0076* (2013.01)

(58) Field of Classification Search
USPC ....................................................... 700/223
See application file for complete search history.

(56) References Cited

U.S. PATENT DOCUMENTS

| | | |
|---|---|---|
| 4,972,657 A | 11/1990 | McKee |
| 5,720,154 A | 2/1998 | Lasher |
| 5,797,515 A | 8/1998 | Liff |
| 5,839,257 A | 11/1998 | Soderstrom |
| 5,946,883 A | 9/1999 | Yuyama |
| 6,003,006 A | 12/1999 | Colella |
| 6,212,855 B1 | 4/2001 | Yasunaga |
| 6,330,351 B1 | 12/2001 | Yasunaga |
| 6,644,504 B2 | 11/2003 | Yuyama |
| 7,121,397 B2 | 10/2006 | Yuyama |
| 7,264,136 B2 | 9/2007 | Willoughby |
| 7,792,349 B2 | 9/2010 | Van Den Brink |
| 7,946,101 B1 | 5/2011 | McGonagle |
| 7,946,421 B2 | 5/2011 | Kowalik |
| 7,954,747 B2 | 6/2011 | Chudy |
| 7,971,414 B1 | 7/2011 | McGonagle |
| 8,072,590 B2 | 12/2011 | Ackley |
| 8,109,066 B2 | 2/2012 | Leu |
| 8,146,747 B2 | 4/2012 | Luciano |
| 8,266,878 B2 | 9/2012 | Luciano |

(Continued)

*Primary Examiner* — Kyle O Logan
(74) *Attorney, Agent, or Firm* — McDonald Hopkins LLC

(57) ABSTRACT

A method and system for inputting, verifying, and communicating order data associated with a patient that may include an order for a patient to take a plurality of medications at various times of the day. The system includes an array of a medication sorting devices configured to communicate with a tracking system for receiving an order and dispensing a plurality of medicaments into a plurality of aligned pouches associated with the order information. The tracking system includes an optimization engine for selecting a medication sorting device to process each order to process a high volume of orders. An inspection assembly that is configured to analyze the plurality of medications within the medication pouches to detect and compare with the order information. The plurality of pouches may be arranged into a dispense package to dispense each pouch as arranged by the order information including medication type, dosage, and time.

14 Claims, 7 Drawing Sheets

(56) References Cited

U.S. PATENT DOCUMENTS

| | | |
|---|---|---|
| 8,639,554 B2 | 1/2014 | Helmus |
| 8,640,747 B2 | 2/2014 | Takafumi |
| 8,712,582 B1 * | 4/2014 | Luciano, Jr. ........ G06F 19/3462 |
| | | 700/236 |
| 8,713,897 B2 | 5/2014 | Luciano |
| 8,777,012 B2 | 7/2014 | Luciano |
| 8,789,700 B2 | 7/2014 | Luciano |
| 9,238,518 B2 | 1/2016 | Luciano |
| 2003/0200726 A1 | 10/2003 | Rast |
| 2006/0271237 A1 | 11/2006 | Kim |
| 2010/0145500 A1 | 6/2010 | Luciano |
| 2012/0081225 A1 | 4/2012 | Waugh |
| 2013/0000260 A1 | 1/2013 | McErlean |
| 2013/0018503 A1 | 1/2013 | Carson |
| 2013/0282163 A1 | 10/2013 | Brown |
| 2015/0353219 A1 * | 12/2015 | Kohl ................... B65B 69/0058 |
| | | 53/473 |

\* cited by examiner

Patient Name — ☐ IMA SAMPLE         1/1
Day and Time of Administration — ☐ *Take Saturday    Morning*
Medication Name, Strength and Dosage — Amlodipine        10MG    X1
*white round G1540 10*
☐ Aspirin EC        81MG    X1
*yellow round A*
Docusate        100MG    X1
*Red P51*
Fluoxetine    20mg        X2
*yellow/green cap PLIVA 6*
Pill Description — ☐ Gabapentin    100mg    X1
*white capsule IP 101 IP 1*
*ExactCare 216-369-2200 E:04/08/14*

— Free Service, Delivered to Your Door
— No More Sorting Bottles
— No More Calling in Refills
— No More Trips to the Pharmacy
— No Missed Doses
— Accurate and Safe

MEDICATION SORTING AND PACKAGING SYSTEM AND METHOD

CROSS-REFERENCE TO RELATED APPLICATIONS

This application claims the benefit of priority of U.S. Provisional Patent Application Ser. No. 62/243,329 filed on Oct. 19, 2015, which is hereby incorporated by reference in its entirety.

FIELD OF THE INVENTION

The present invention relates generally to a system and method of sorting and packaging medications, and more particularly to a system and method for producing a high volume of individualized custom dispensing packages containing a combination of various medications or supplements organized according to a dosing schedule.

BACKGROUND

Individuals may be subject to being prescribed or otherwise taking a variety of medications and supplements. These "medicaments" may each have unique requirements especially regarding the type, concentration, amount, and dosing schedule. A user that is consuming these medicaments is usually required to maintain their own dosing schedule either with the assistance of separator containers or on their own ability.

As such, various services have become available to users that take a variety of medications or supplements. These services are designed to identify the type and quantity of medicaments, sort the medicaments, and individually package medicaments in a dispensing container subject to the dosing schedules of the individual. One such service is provided by ExactCare Pharmacy of Valley View, Ohio.

ExactCare Pharmacy provides a service that organizes medicaments into individualized packages convenience for a user. The medicaments are organized by quantity, amount, and dosing schedule and arranged in a dispensing container. However, as this service has become more desirable, the provider is required to increase the amount and number of dispensing containers produced. The scalability of increased production may be subject to variables, which if mismanaged, may cause delays due to the nature of quickly organizing a variety of medicaments, script validations, changes in patient orders, non-routine requests, refill authorizations, and a variety of other elements that may be considered to properly execute a high volume medicament packaging service.

Inefficiencies are undesirable from a productivity perspective. Therefore, there is a need for a method and system that is configured to optimize the production of sorting and packaging medicaments into dispensing containers to produce a high volume of individually customizable dispensing packages.

SUMMARY

Provided is a method for packaging a high volume of customizable dispense packages having a plurality of aligned pouches for containing medicaments including indicia having medicament information and dosing schedule. The method including the steps of inputting a plurality of order data including at least a first order and a second order into a tracking system. The order data may include patient identification information, insurance information, and hospital or doctor information. The order data may also include the type of medicaments, amounts, prescriptions, and dosing schedule. The order data may be inputted directly by the individual or from a third party provider such as a nursing home, hospital, doctor, nurse or other healthcare professional. The order data may be independently verified to confirm prescriptions and proper payment arrangements.

The tracking system may be in communication with an array of medication sorting devices. One of an array of medication sorting devices is selected for processing the first order data and another medication sorting device is selected for processing the second order data. The selection may be based on the current status of each of the medication sorting devices within the array wherein each status may include a determination of the amount and type of medicaments contained within the device at the time the first and second order data is to be processed. The first order data may then be transferred from the tracking system to a selected medication sorting device. The second order data may then be transferred from the tracking system to a selected medication sorting device. The medication sorting devices of the array may each be stocked with a plurality of medicaments and the tracking schedule may analyze the status of the array of medication sorting devices to determine which device is to process which order. The devices may dispense medicaments into a plurality of pouches associated with the data. The plurality of pouches may be transferred to an inspection assembly configured to detect the plurality of medicaments within the pouches and to verify the order data corresponds to the medicaments within the pouches.

In another embodiment, disclosed is a system for packaging a high volume of customizable dispense packages having a plurality of aligned pouches for containing medicaments including indicia having medicament information and dosing schedule. A tracking system includes a database for inputting, verifying, and communicating order data associated with a patient that may include an order for a patient to take a plurality of medications at various times of the day. The system includes an array of a medication sorting devices configured to communicate with the tracking system for receiving an order and dispensing a plurality of medications into a plurality of medication pouches associated with the order data. The pouches may be sent to an inspection assembly that is configured to analyze the plurality of medications within the medication pouches to detect and compare with the order data. The inspection assembly may be configured to notify that the medication pouches are accepted or rejected. If rejected, corrections may be made to add or remove medicaments from the pouches as needed. The plurality of pouches may be arranged into a medication dispense package that is configured to dispense each pouch as arranged by the order information including medication type, dosage, and time.

BRIEF DESCRIPTION OF THE DRAWINGS

The disclosed method and system may be better understood by reference to the following detailed description taken in connection with the following illustrations, wherein:

FIG. 7 illustrates a view of a pouch with medicaments having indicia thereon.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
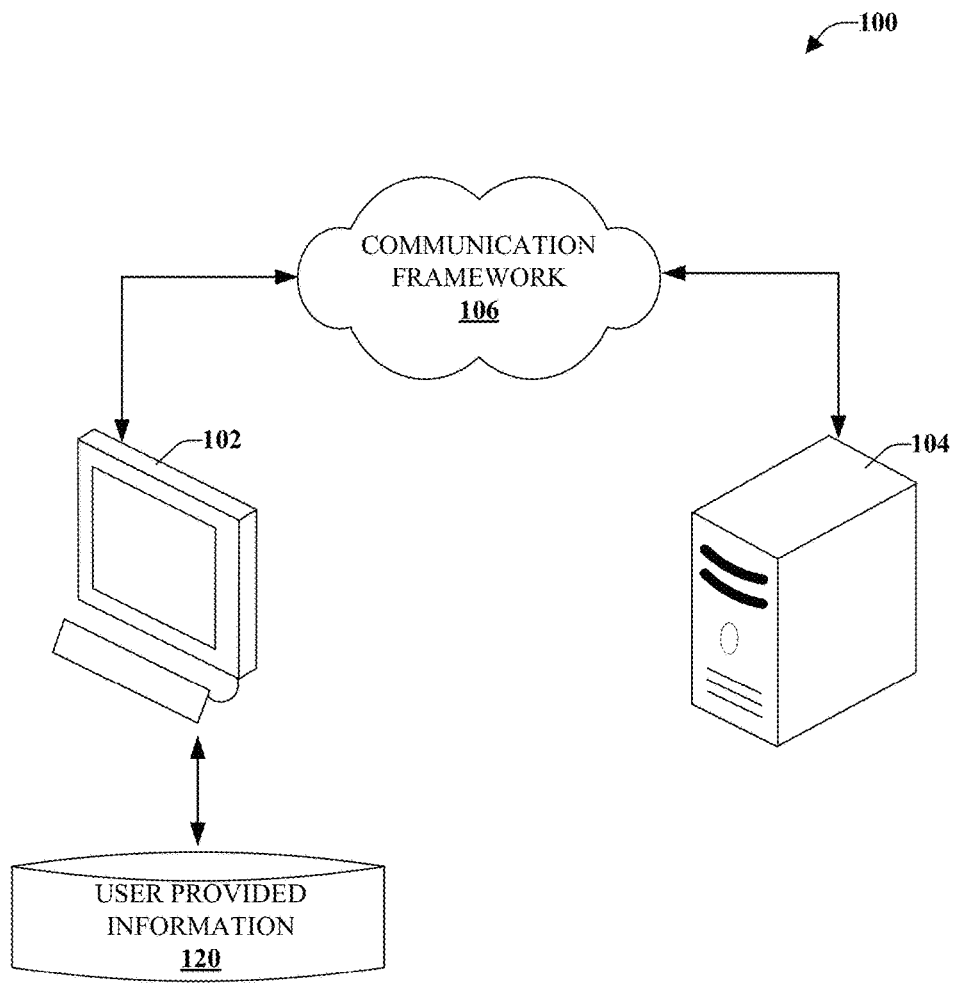
FIG. 1 is a schematic diagram of embodiments of a tracking system for inputting data representative of a plurality of orders in accordance with the present disclosure.

FIG. 1 illustrates a system architecture 100 that may implement the system and method of the present disclosure. In particular, a user display 102 may be in communication with a computer/processor 104 by way of a communication framework 106 such as the internet, network, or cloud as is generally known in the art. The display 102 is accessible by an individual to access a database to input order data to order a dispensing package and other medicaments from the service. The individual may be prompted to input order data 120 at the display 102. The order data 120 may include a name, date, age, address, health care provider information, patient identification information, insurance information, and hospital/doctor information or other data required to generate the order. The order data may also include the type of medicaments, amounts, prescriptions, and dosing schedule. The order data may be inputted directly by the user or from a third party provider such as a nursing home, hospital, doctor, nurse, pharmacist, or other healthcare professional.

Figure 2:
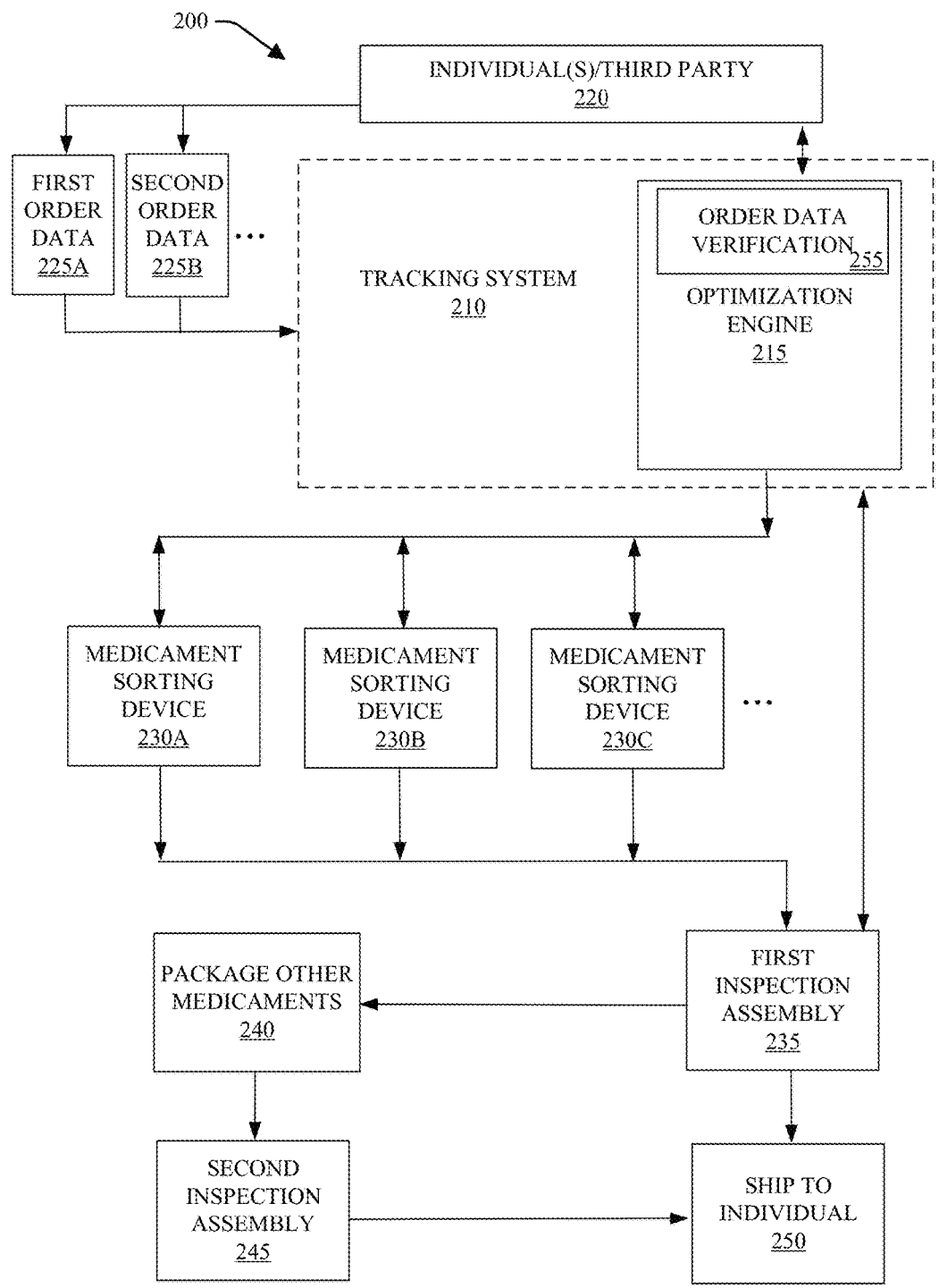
FIG. 2 is a flow chart of embodiments for a system and method for sorting and packaging medicaments into dispensing packages in accordance with the present disclosure.

FIG. 2 illustrates an embodiment of the instant system 200 of the present disclosure. It is to be understood, that the system 200 is configured to process a high volume of orders wherein a plurality of individuals or third parties 220 may input order data 225A, 225B representative of their respective order for a medication dispenser package and/or other medicaments. This system 200 is particularly designed to efficiently process a high volume of orders in a short amount of time. In particular, the system 200 may process over about 50,000 orders within about an 8 hour period. The system 200 may process over about 100,000 orders within about an 8 hour period and may even process over 250,000 orders up to about 500,000 orders within about an 8 hour period.

The orders may include at least a first order 225A and a second order 225B wherein the individual 220 inputs them into a tracking system 210 by the system architecture 100. The tracking system 210 may be a software program that maintains communication with an array of medication sorting devices 235A, 235B, and 235C over the communication framework 106. The tracking system 210 may include an optimization engine 215 that is configured to constantly monitor and communicate with the array of medicament soring devices 230A, 230B, and 230C. There may be any amount of medicament sorting devices as there may be 2, 3, 4, 5, 6, 7, 8, 9, 10 or more and this disclosure is not limited. The medicament sorting devices may be a particular device configured to store and sort medicaments into a individual pouches aligned with one another and configured for packaging. The medicament sorting devices may also be configured to print label indicia on the pouches containing the medication. One such example of a medicament sorting device is the ATP®2 manufactured by TCGRx. This device may be configured to maintain up to 480 different canisters of medicaments in each unit. Each canister may be configured to store a different type or sized medicament that is to be dispensed into each pouch while also being counted, tracked and communicated to the tracking system 210. However, this system is not limited to this device as any other type of medicament sorting device may be incorporated herein. The system 200 may be scalable wherein any number of medicament sorting devices may be used for high volume process periods and for low volume process periods.

The tracking system 210 monitors the array of medicament sorting devices and tracks the remaining amount of medicaments remaining within each canister within the device. The optimization engine 215 compares the information from the plurality of orders including at least the first order data 225A and the second order data 225B along with the status information of each of the medicament sorting devices 230A, 230B, 230C. In one embodiment, one of the medicament sorting devices within the array is selected by the optimization engine 215 to process the first order data 225A and the tracking system 210 sends the first order data 225A to the selected medicament sorting device 230A. Another medicament sorting device 230B is selected to process the second order data 225B and the tracking system 210 sends the second order data 225B to the selected medicament sorting device 230B to be processed. It should be understood that there are many variables associated with the selection step as the optimization engine 215 may be in constant communication with the array of medicament soring devices to properly analyze and select which order is to be processed by which device.

There exist many types, sizes and combinations of medicaments and the array of medicament sorting devices may have various medications within the canister. Each selection is premised on the status of the device as the time the order data is to be processed. This functionality may allow for the method and system to process a high volume of orders. Additionally, the tracking system 210 may be configured to provide notification when a particular canister or device is running low on medicaments and is to be refilled. The optimization engine 215 may reduce the amount of time required to process orders to allow patients to receive the dispense packages with accuracy and in a timely manner.

The medication sorting devices 230 may fill a plurality of pouches 310 with medicaments and print label indicia (FIG. 7) along the side of the pouches 310. The processed pouches 310 may then be transferred to a first inspection assembly 235. The first inspection assembly 235 may include at least one mechanism that is configured to wind and unwind the pouches 310 and align the plurality pouches 310 with a camera. The mechanism may translate the plurality of pouches 310 relative to the camera such that camera may capture images of the plurality of pouches 310 with the medicaments and labels printed thereon. The first inspection assembly 235 may be in communication with the tracking system 210 to verify the order data associated with the processed pouches 310. The first inspection assembly 235 may display a video feed or still images of the pouches at a display window to allow a worker to manually inspect the medications for damage and accuracy.

Alternatively, the first inspection assembly 235 may automatically identify if the medicaments are accurately placed in a correctly labeled pouch, verify that the medicaments in the pouch are in accordance with the respective order data, or identify if medicaments are damaged or need to be replaced. In one embodiment, the pouch inspection assembly 235 may be an apparatus called the Photon™ that is manufactured by a company named Zius. However, this system 200 is not limited to this inspection assembly as any other type of inspection assembly may be incorporated herein.

Figure 3:
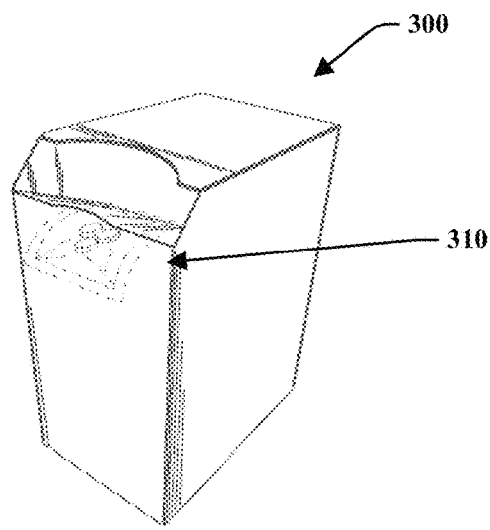
FIG. 3 is a perspective view of an embodiment of a dispensing package.
Figure 4:
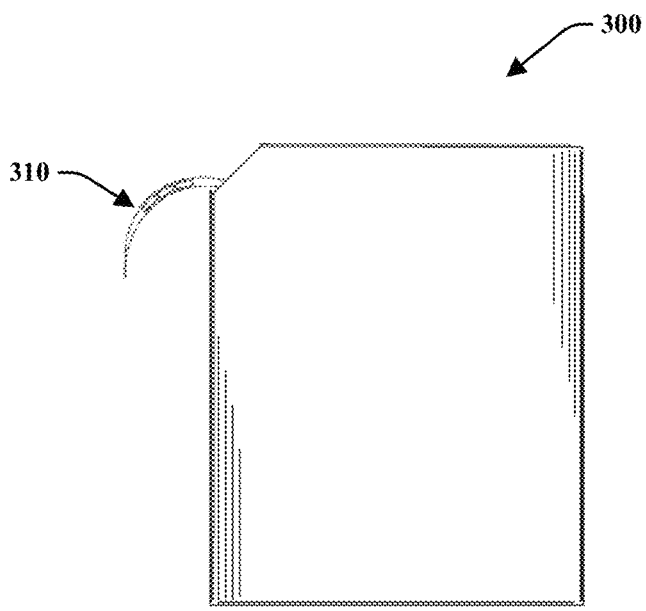
FIG. 4 is a side view of the dispensing package of FIG. 3.
Figure 5:
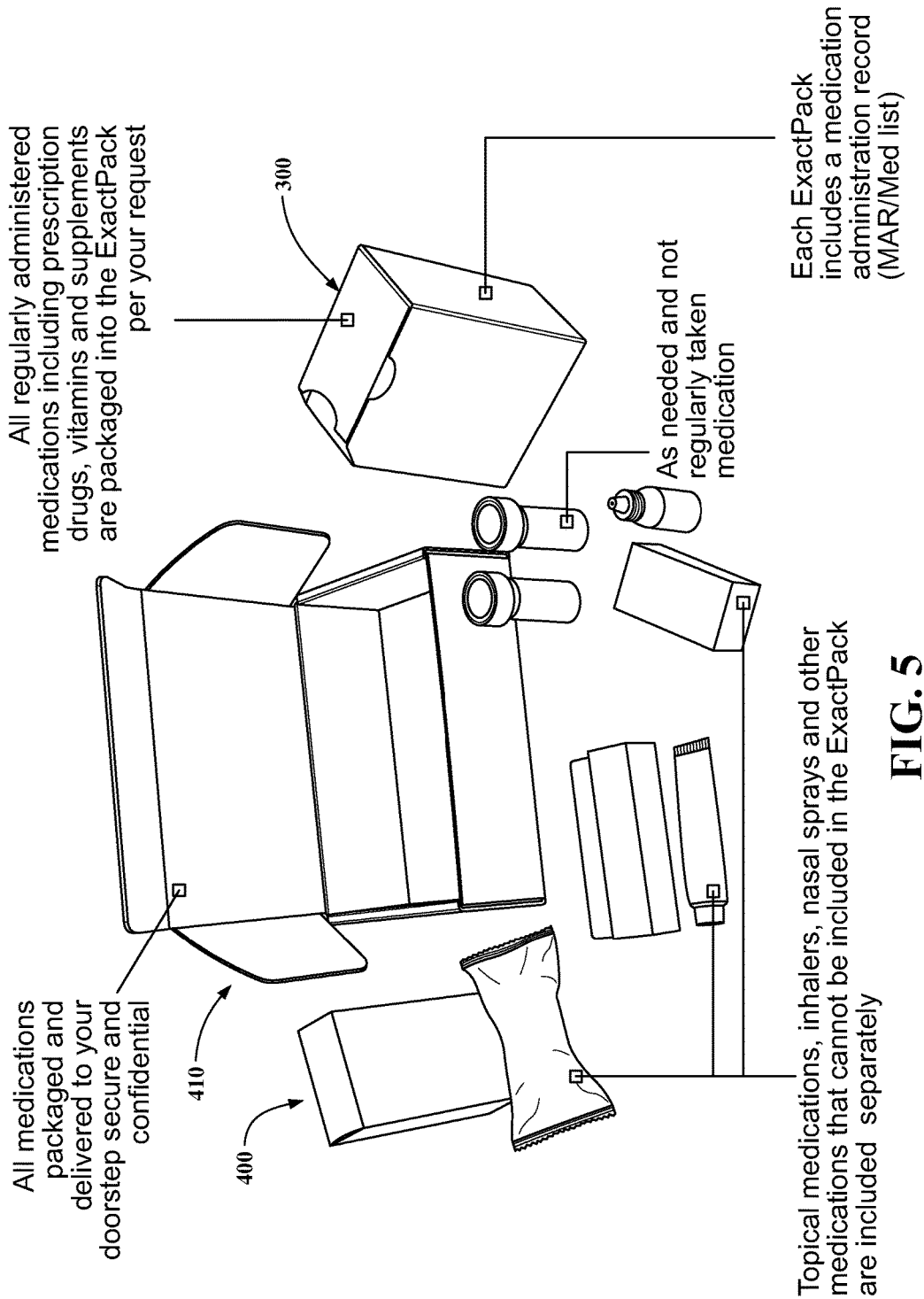
FIG. 5 is an illustration of the dispensing package that may be shipped in a container along with other medicaments in accordance with the present disclosure.

After inspection, the plurality of pouches 310 may be placed in a dispense package 300 as illustrated by FIGS. 3, 4, and 5. The dispense package 300 may be configured to individually dispense each pouch 310 in accordance with the dosing schedule identified by the respective order data. However, the order data may also includes "non-routine" medicaments 400 such as liquids, ointments, inhalers, or other type of medication or supplement. "Non-Routine" medicaments may be medicaments that do not fit within the pouches 310 or may be taken on an as needed basis per the respective order data. The dispense package 300 may be placed in a container 410 and transferred to another workstation 240 that may provide these non-routine medicaments 400 (FIG. 5). A worker may view the respective order data from a workstation and select the non-routine medicaments 400 from a shelving unit. Alternatively, the workstation 240 may include an automated shelving unit 610 wherein the shelving unit may be configured to automatically identify and dispense non-routine medicaments 400 to be placed into the container 410 with the dispense package 300 therein to complete the order associated with the order data. The container 410 may then be transferred to a second inspection assembly 245 wherein a worker may confirm its contents prior to shipment to the individual 250.

Figure 6:
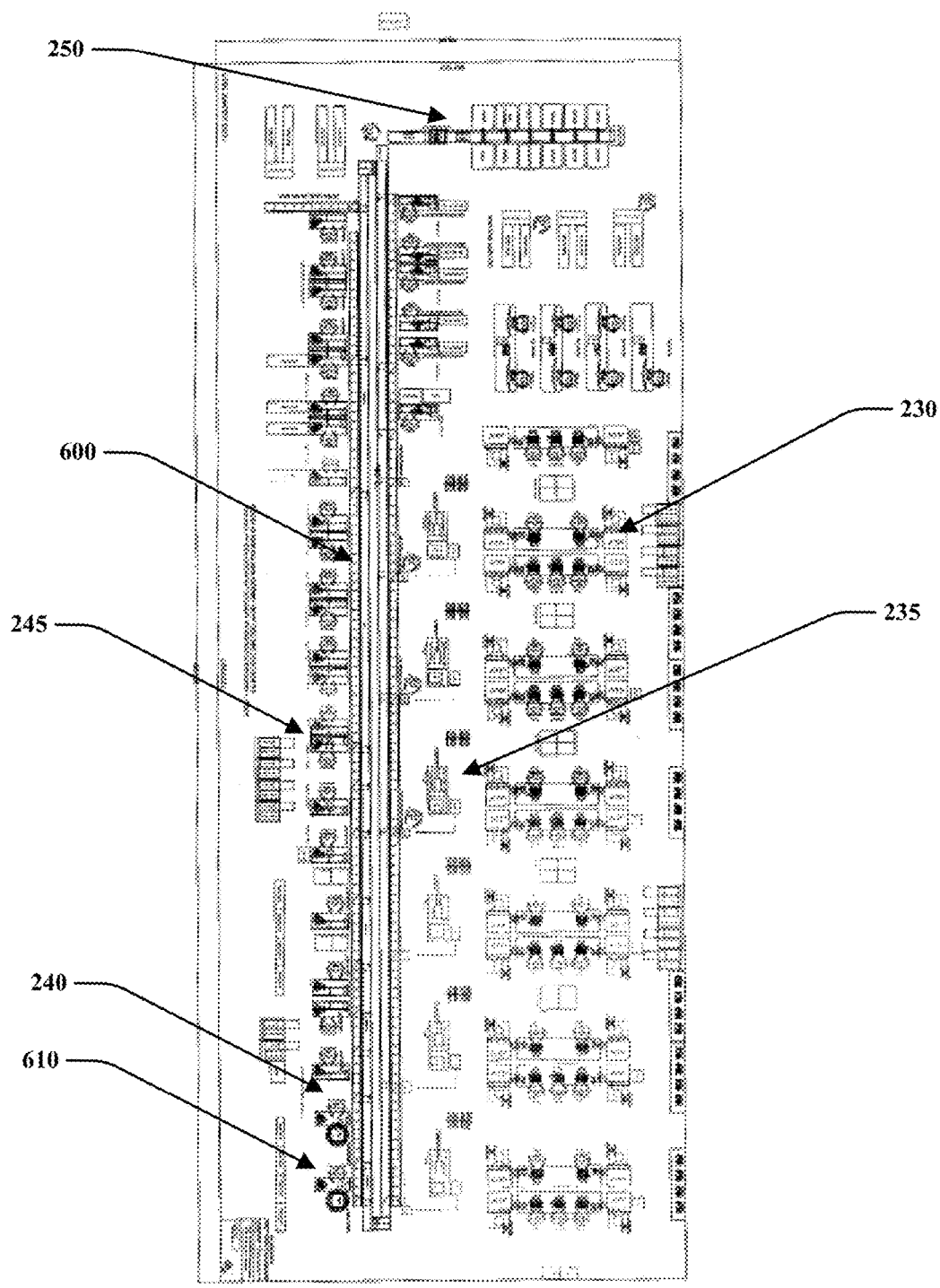
FIG. 6 is a plan view of embodiments of a workflow assembly of various stations of the method and system in accordance with the present disclosure.
Figure 8:
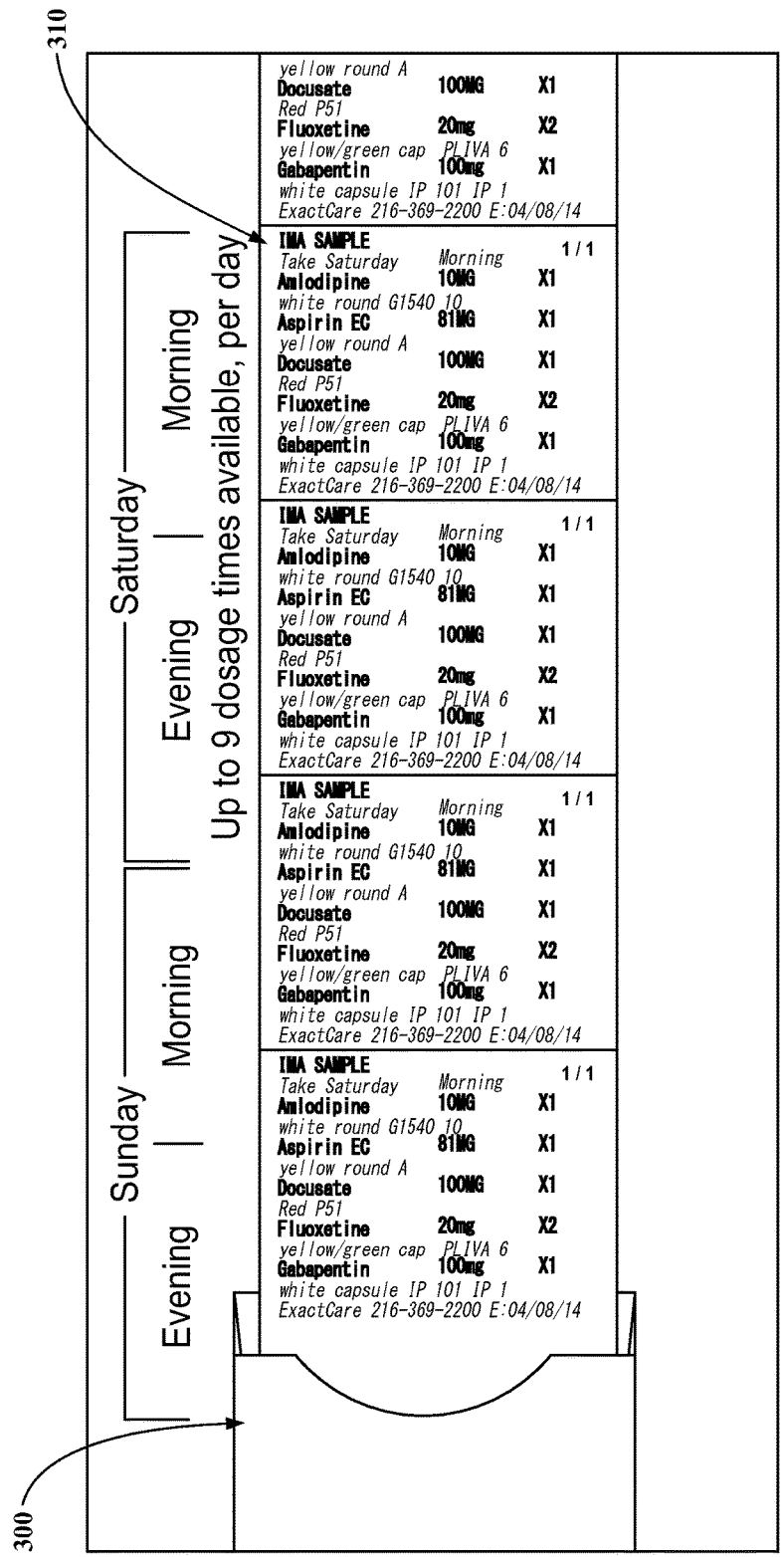
FIG. 8 illustrates a plurality of aligned pouches dispensed by the dispense package in accordance with the present disclosure.

As illustrated by FIG. 6, the container 410 may be a box or otherwise be a bin that is configured to maintain the contents while translating along a conveyor system 600 from workstation to workstation. Further, this system 200 may include other workstations for printing labels or for verifying contents within the containers on the conveyor system.

This process may be operated in a continuous manner and include a workflow process arrangement as illustrated by FIG. 6. Here, the floorplan of a production assembly is provided having a plurality of medicament sorting devices 230 along with a plurality of stations 235, 240, 245 set up along the conveyor system 600 for inspections and to place non-routine medications within a container 410 associated with the respective order data. The dispense package 300 and non-routine medicaments 400 may then be shipped to the individual. In one embodiment, the tracking system 210 may be in communication with each station to allow a worker to verify the contents of the container 410 and dispense package 310 to insure conformity with the order data. This system 200 is configured to process a high volume of customizable dispense packages having a plurality of aligned pouches 310 containing medicaments including indicia having medicament information and dosing schedule.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

I claim:

1. A method of processing orders for customized medicament packages, the method comprising:
    inputting at least a first order data and a second order data into a tracking system having an optimization engine;
    verifying the first order data and second order data with a third party;
    analyzing an array of medicament sorting devices by the optimization engine;
    selecting a medicament sorting device from the array of medicament sorting devices by the optimization engine for processing the first order data and the second order data;
    processing the first order data at a first medicament sorting device to package a plurality of medicaments in a first plurality of aligned pouches; and
    processing the second order data at a second medicament sorting device to package a plurality of medicaments in a second plurality of aligned pouches wherein the first order data and second order data is representative of an order for a medication dispenser package or medicament wherein the method is configured to process over 50,000 orders within about 8 hours.

2. The method of claim 1 further comprising inspecting the first plurality of aligned pouches at a first inspection assembly.

3. The method of claim 2 further comprising inspecting the second plurality of aligned pouches at a second inspection assembly.

4. The method of claim 1 further comprising placing the first plurality of pouches in a dispense package.

5. The method of claim 4 further comprising placing the second plurality of pouches in a dispense package.

6. The method of claim 4 further comprising selecting non-routine medicaments to be packaged and shipped to an individual with the dispense package.

7. The method of claim 1 wherein the method is configured to process over 250,000 orders up to 500,000 orders within about 8 hours.

8. The method of claim 1 wherein the order data is at least one of a type of medicament, amount, prescription, and dosing schedule.

9. A system for processing orders for customized medicament packages, the system comprising:
    a tracking system for receiving a plurality of order data from a plurality of individuals or third parties, the tracking system including an optimization engine wherein the optimization engine is configured to compare information from the plurality of order data, wherein the order data is representative of an order for a medication dispenser package or medicament; and
    an array of medicament sorting devices each configured to place a plurality of medicaments into a plurality of aligned pouches associated with an order data, wherein the optimization engine is configured to communicate with the array of medicament sorting devices to analyze and select the medicament sorting device to an order wherein the system is configured to process over 50,000 orders within about 8 hours.

10. The system of claim 9, further comprising at least one inspection assembly that is configured to analyze the plurality of medicaments within the plurality of pouches to detect and compare with the associated order data.

11. The system of claim 10, further comprising a dispense package configured to receive the plurality of pouches and to dispense each pouch as arranged by the order information including medication type, dosage, and time.

12. The system of claim 10, further comprising a conveyor system for translating the dispense packages from the inspection assembly to a non-routing medicament workstation.

13. The system of claim 9 wherein the system is configured to process over 250,000 orders up to 500,000 orders in a span of about 8 hours.

14. The system of claim 9 wherein the order data is at least one of a type of medicament, amount, prescription, and dosing schedule.

* * * * *